United States Patent
Farr, II et al.

(10) Patent No.: US 6,699,252 B2
(45) Date of Patent: Mar. 2, 2004

(54) METHODS AND INSTRUMENTS FOR IMPROVED MENISCUS TRANSPLANTATION

(75) Inventors: Jack Farr, II, Greenwood, IN (US); James M. Gross, Gainesville, FL (US)

(73) Assignee: Regeneration Technologies, Inc., Alachua, FL (US)

( * ) Notice: Subject to any disclaimer, the term of this patent is extended or adjusted under 35 U.S.C. 154(b) by 0 days.

(21) Appl. No.: 09/836,099

(22) Filed: Apr. 17, 2001

(65) Prior Publication Data

US 2002/0151975 A1 Oct. 17, 2002

(51) Int. Cl.⁷ .............................. A61B 17/32; A61F 5/00
(52) U.S. Cl. ...................... 606/79; 623/14.12; 606/86
(58) Field of Search .................... 606/79; 623/14.12, 623/23.72, 908

(56) References Cited

U.S. PATENT DOCUMENTS

| | | | | |
|---|---|---|---|---|
| 5,158,574 A | * | 10/1992 | Stone | 264/108 |
| 5,263,498 A | * | 11/1993 | Caspari et al. | 128/898 |
| 5,681,320 A | * | 10/1997 | McGuire | 606/104 |
| 5,800,437 A | | 9/1998 | Gustilo et al. | 606/86 |
| 5,916,218 A | | 6/1999 | Hagen et al. | 606/82 |
| 5,980,526 A | * | 11/1999 | Johnson et al. | 606/86 |
| 6,022,353 A | | 2/2000 | Fletcher et al. | 606/79 |

* cited by examiner

Primary Examiner—Cary E. O'Connor
Assistant Examiner—Candice C. Melson
(74) Attorney, Agent, or Firm—McAndrews, Held & Malloy, Ltd.; Donald J. Pochopien

(57) ABSTRACT

Improved methods of, apparatuses, devices and kits are disclosed for preparing and implanting a meniscal implant by surgical means into a recipient in need thereof. The bone bridge of the replacement meniscus is pre-shaped to fit into a slot in the recipient's tibia. The positioning of the slot is accomplished by an alignment procedure that conforms the slot to the angle of the dorsal tibial plane. Also disclosed are devices and corresponding methods to size the bone bridge section of the implants that have improved efficiency and increase the quality of implant and success of meniscal implant procedures.

13 Claims, 9 Drawing Sheets

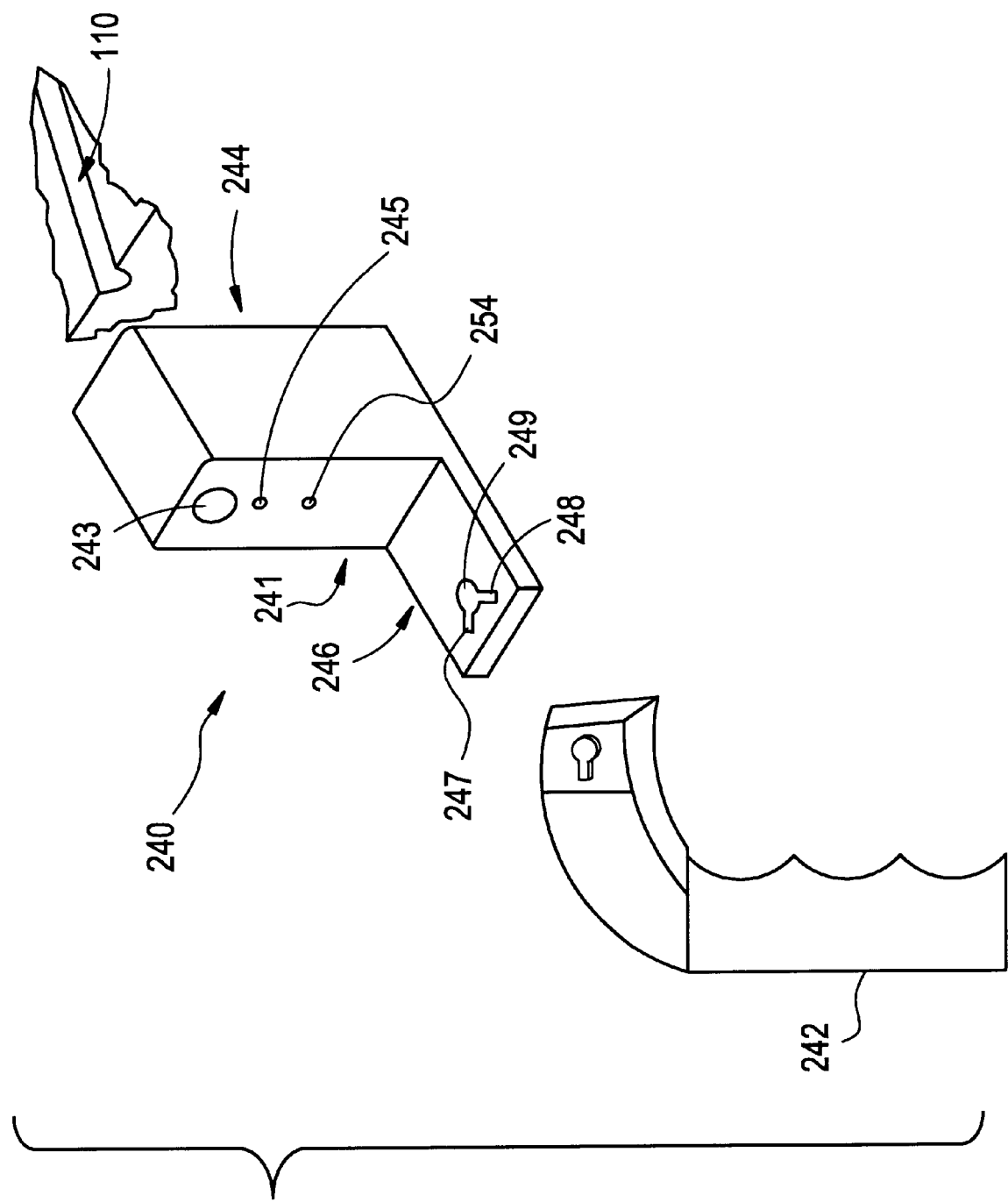

METHODS AND INSTRUMENTS FOR IMPROVED MENISCUS TRANSPLANTATION

BACKGROUND OF THE INVENTION

Orthopedic surgical procedures for knee meniscus replacement have improved over the years, concurrent with improvements in surgical instruments, expertise, and suitable materials. Although some injuries to a meniscus may be repaired, symptomatic biomechanical loss of meniscal function may indicate the need for a meniscal replacement procedure.

Each knee has two menisci, a lateral and a medial meniscus. Each meniscus is a crescent-shaped fibrocartilaginous tissue primarily attached to the tibial bone at an anterior and a posterior horn. The menisci deepen and cushion the receiving area of the tibia, into which two condyles of the femur transfer the weight of the erect human body. The meniscus acts to increase the contact area, provide cushion at impact and may play a role in articular cartilage nutrition.

Meniscus transplantation has become a commonly offered option for patients experiencing symptoms secondary to the absence of meniscus. One goal of the present meniscus transplantation invention is to improve the efficiency of the surgery, and maintain reproducibility and quality. Another goal, to assist in this allograft technique, is to provide a system of instruments to assist in position planning followed by fixation.

Recently one supplier of allograph tissue obtained from cadaver donation, Regeneration Technologies, Inc., has offered pre-sized meniscus allografts. Review of the limited meniscal allograft basic science literature suggests that soft tissue fixation alone is sub-optimal, and that bony fixation appears to assist in reduplication of hoop stresses. This reduplication of the biomechanical effects of a meniscus is essential to restore function. The allografts available from Regeneration Technologies have the capability of use for bone bridge and bone plug techniques. The bone plug technique is well described in the literature, and the present invention introduces new modifications to the bone bridge concept.

The present invention relates to an innovative procedure, system, kits, and related instruments, for the replacement of a knee meniscus using an allograft or xenograft meniscus, connected to a bone section, obtained from a donor. One reason for development of this invention is that, despite realized advantages from existing methods, there have been some difficulties encountered with utilizing meniscus implants. For example, surgical procedures involving transplantation and fixation of these implants can be tedious and lengthy. Currently, the bones involved in meniscus replacement surgery must be specifically shaped for the recipient during surgery. This can require up to or over an hour of surgical time.

Two common approaches to meniscus replacement are the keyhole surgical technique and the double bone plug technique. The keyhole technique uses a keyhole guide having a posteriorly placed pin to establish an orientation for a guide pin. The pin is driven into the anterior face of the tibia, and a reamer is used to drill out bone around this pin, forming the wider area of the keyhole. In this method, fluoroscopy could be used to verify that the pin lies parallel to the tibial plateau. That is rarely the practice. However, there is no direct visual method to ascertain correct placement when using this approach. Next, a ronguer or burr is used to open a slot to the top of the tibia to complete the keyhole-shaped slot. In subsequent steps, allograft or xenograft tissue comprising bone attached to a replacement meniscus is shaped so the bone fits the keyhole. This may require considerable crafting during the surgical period, and because of the need to custom-fit the implant to the surgically created keyhole, the implant generally cannot be fashioned to a precise fit prior to initiation of the surgical procedure. Once shaped to fit the keyhole, this tissue is slid into place in the tibia, and the operation is concluded.

For the double bone plug technique, the bone attaching to the anterior and posterior meniscus horn attachments are shaped into circular bone plugs. A guide, such as an ACL guide, is used to position the posterior hole socket in the tibia to receive the posterior plug. The posterior plug is secured into this socket, the graft is positioned, and a hole is made for the anterior plug. The anterior plug then is secured in place, and the operation is concluded.

In both of the above techniques, the surgical team is required to make substantial modifications to the xenograft or allograft implant to custom fit it to the particular recipient's requirements. Despite this often-substantial effort, the result may be sub-optimal, in that the meniscus may not be properly aligned to the tibial plane. Also, particularly with the keyhole technique, breaks occur at an undesirable frequency either in the insert or the keyhole during insertion.

Surgeons have also been known to insert the xenograft or allograft meniscus implants by making a slot in the tibia and fitting a rectangular donor bone section into the slot. However, these operations are conducted without instruments specifically designed for this procedure.

The present invention discloses a technique and instrumentation with which to carry out meniscal transplants more effectively and efficiently. Thus, one advantage of the present invention is to improve the quality and long-term results of meniscal transplants by improving the accuracy and stability of the meniscus placement. Another advantage of the present invention is improving the ease of the procedure through the use of specific instruments and through the use of a specific procedure in which a pre-shaped implant may be lodged at an implant site of easily and precisely created and reproduced geometry. These improvements result in less time spent custom-fitting a meniscus implant, and in a more stable implant.

SUMMARY OF THE INVENTION

The present invention presents an advance in the method of insertion of an allograft or artificial composite (e.g. allograft bone with integrated SIS CMI, etc.) or xenograft meniscus implant to replace a damaged meniscus in a recipient. Embodiments of a method for the insertion are described, and specific instruments used in the method are described. These instruments facilitate an easier and more efficient surgery for meniscus replacement using the insertion method of the present invention.

In one embodiment of a method of this invention, after exposing the tibia superior surface, a linear shallow groove, or reference slot, is made between and encompassing the anterior and posterior meniscus horn attachments. One way to make the reference slot is with an arthroscopic burr. After a reference slot is formed with a relatively straight and flat bottom, a depth gauge is placed into the reference slot. The distance between the top edges of the gauge at anterior and posterior points, relative to the walls of the groove at these points, are compared. If these are not evenly aligned, such that the same gap exists from front to back between the top of the depth gauge and the top of the reference slot, the gauge is removed and the bone material causing high spot(s) and mal-alignment in the slot is removed, for example, with an arthroscopic burr. This assessment with the depth gauge, and the additional removal of material, are repeated until a groove exists that has a level bottom angled parallel to the tibial slope.

The depth gauge is then re-inserted into the groove, and preferably is stabilized in position, at least partly, by a distal section of the gauge that extends downward over the posterior end of the tibia and purchases onto the posterior margin of the tibia with one tooth, or like means. With the gauge so positioned in the groove, the gauge's anterior to posterior ("AP") "lie" mimics that of the tibial slope. A drill guide is placed over the depth gauge at its anterior end. The drill guide is used to position and properly angle a drill bit, which forms a hole for a guide pin. Once the guide pin is set into that hole in the tibia, the guide pin is used as a reference for one of several means to create a slot between the guide pin upward to the reference slot. Once the slot is formed, a sized bone bridge integral with the replacement meniscus (where the horns of said meniscus are attached at the bone bridge's superior surface) is slid into the slot. As will be described herein, a bone bridge is a segment of donor bone that includes the attachment horns of the meniscus from said donor, and which has been sized to fit the slot in the recipient's tibia. After alignment of the bone bridge, a pin, screw, suture, or other attaching means stabilizes the bone bridge with the tibia.

In another embodiment, the present invention is directed to a kit for use in a meniscal transplant (implant). In its broadest aspect, the kit comprises a bone bridge sizer; and instructions for use of said bone bridge sizer to cut a bone bridge of a meniscus implant. In one embodiment, the above-described kit also includes a tool to size a slot in a tibia bone, the tool being selected from the group consisting of a slot sizer, a rasp, and a box chisel. In yet another embodiment, the kit of the present invention includes a drill pin and a cannulated drill bit sized to fit over the drill pin. In a further embodiment, the kit comprising a bone bridge sizer and instructions also includes at least one pre-sized meniscus implant.

Additional objects, advantages, and novel features of the invention are set forth in the description which follows, from which such advantages will become apparent to those skilled in the art upon examination of the following, or may be learned by practice of the invention according to this disclosure. The objects and advantages of the invention may be realized and attained by means of the instrumentalities and combinations particularly pointed out in the appended claims and equivalents thereof.

BRIEF DESCRIPTION OF THE DRAWINGS

FIG. 2C is a perspective view of a second embodiment of a drill guide utilized in this invention, having additional guide holes to form deeper slots.

DETAILED DESCRIPTION OF THE INVENTION

The foregoing and other objects and advantages are attained by providing a range of possible variations to the basic meniscus replacement method and instruments of the present invention. In the detailed description below, a number of embodiments are described. These are not meant to be limiting in defining the scope and breadth of the present invention. Further, for purposes of this disclosure, a meniscus transplant is taken to mean the same as a meniscal implant, and both terms are defined as a meniscus integrally attached to a section of bone. Also for the purposes of this disclosure, a bone section, also referred to as a bone bridge section, is meant to mean a three-dimensional, six-sided, substantially elongated box-like section of a tibial bone to which is attached a meniscus at one end. This can be roughly, partially, or precisely sized, depending on the context. The preferred attachment between this bone section and the meniscus is the original, integral attachment as found in the donor. Alternately, an attachment is made by means known to those skilled in the art, such as metallic screws, bone screws, sutures, and so forth.

Figure 1A:
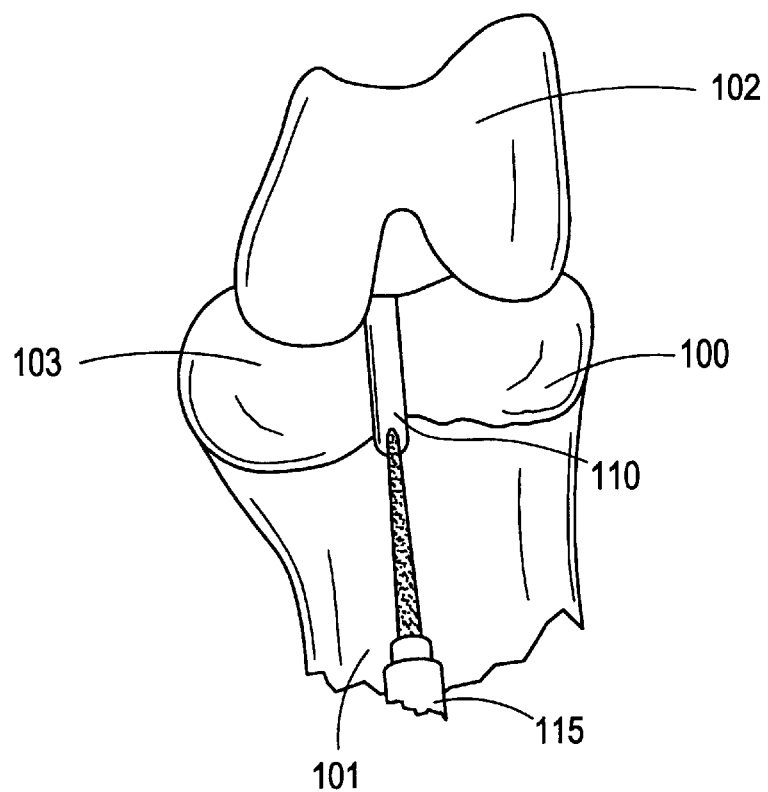
FIGS. 1A through 1H show steps in a preferred embodiment of the method of meniscus implant surgery. It is noted that throughout the figures, like features have the same designated numbers.

Referring to FIGS. 1A through 1H, the following steps describe a general embodiment of the present invention, and the specific preferences and descriptions provide variations of this general embodiment:

1. Following arthroscopic examination and removal, as needed, of the native meniscus and any debris, and after making an anterior incision to access the tibial plateau, 100, a linear reference slot, 110, is created, as by a burr, 115, between and including the anterior and posterior meniscus horn attachment sites. This is shown in FIG. 1A, where the tibia, 101, articulates with the femur, 102. The remaining meniscus (contralateral, intact (non-involved)), 103, is also shown. Preferably, this reference slot is 4 mm deep in subchondral bone. The bottom of the reference slot needs to be level and follows the contours of the tibial anterior to posterior slope. In making this reference slot, the tibial spine is cut through, removing a section of this spine so the base of this portion of the reference slot is in line with the anterior and posterior horn regions of the reference slot.

Figure 1B:
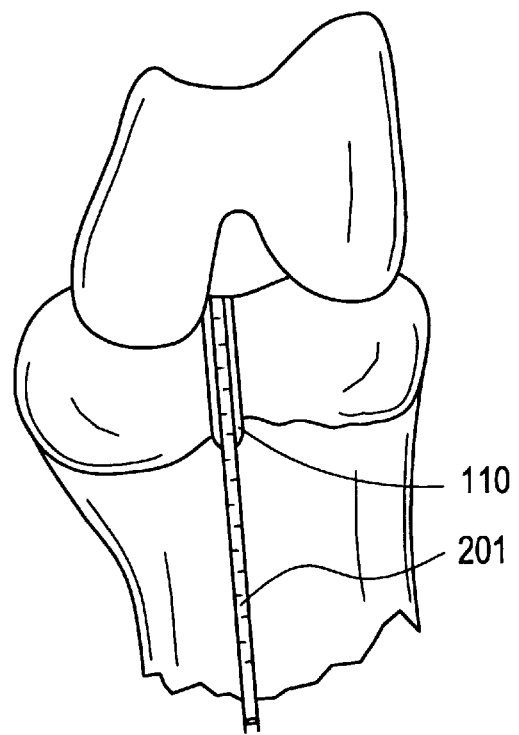
Figure 1C:
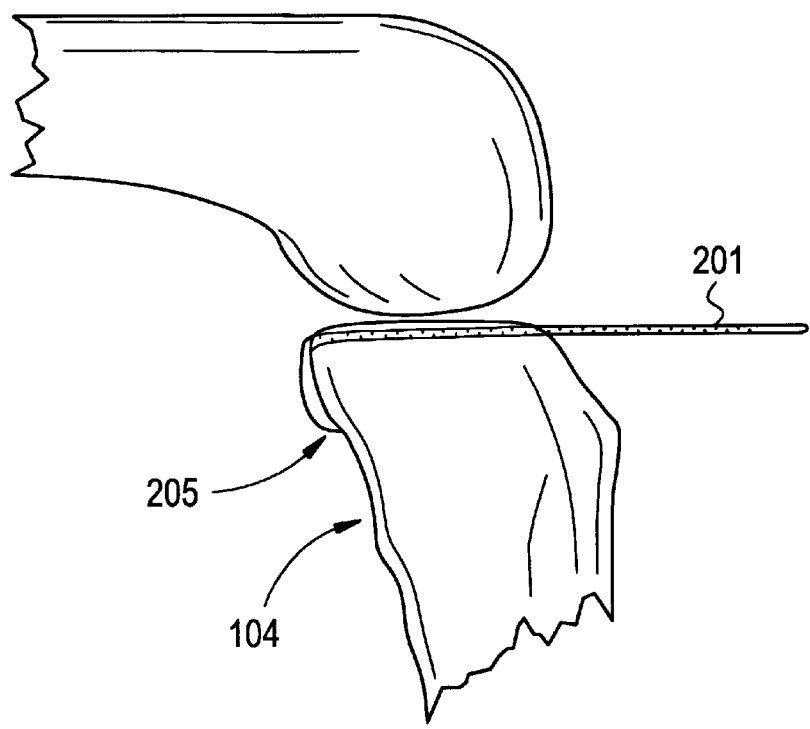

2. A depth gauge, 201, is inserted into the linear reference slot, 110, as depicted in FIGS. 1B and 1C. A preferred embodiment of the depth gauge comprises a straight rod having a section in the reference slot and a section extending anteriorly from the reference slot, a downward-directed end portion directed to the posterior of the tibia, and at least one tooth, or like means, on the end portion disposed toward the tibia.

3. An assessment is made, preferably by eye, comparing the top edge of the straight rod section in the reference slot to the reference slot walls above the rod. This indicates the levelness of the reference slot bottom in relation to the anterior/posterior slope of the tibia. If the rod and reference slot bottom are not properly aligned to this slope, the rod is removed, high areas of bone or overlying cartilage in the reference slot are removed, and the rod is placed back into the reference slot. The levelness assessment is repeated, and additional material is removed as needed until the reference slot bottom is assessed to be in line with the tibial slope.

4. Referring to FIG. 1C, the depth gauge, 201, is temporarily anchored in one place by securing one or more teeth, 205, or like means, of the end portion into the exterior surface of the posterior tibia, 104, in the area directly below and posterior to the reference slot. In a preferred variation of this embodiment, the end of the rod connecting to the end portion is looped upward (See FIG. 2A, 213) to go over the tibial plateau posteriorly to pass over the posterior cortex, where a reference slot is not made. As the reference slot continues to, but not through, the posterior cortex, this loop extends over this remaining 3–5 mm of posterior cortex. This loop then travels down to the end portion bearing at least one tooth. A more basic embodiment does not have this loop, and is used in applications where the reference slot passes through the posterior cortical wall of the tibia. In a preferred embodiment of the method, downward and forward pressure is exerted to keep this tooth engaged, and to keep the depth gauge flatly aligned to the bottom of the reference slot.

Figure 1D:
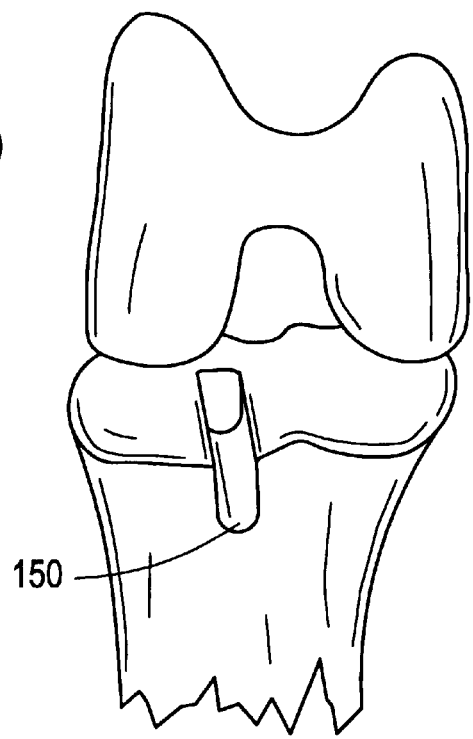
Figure 1E:
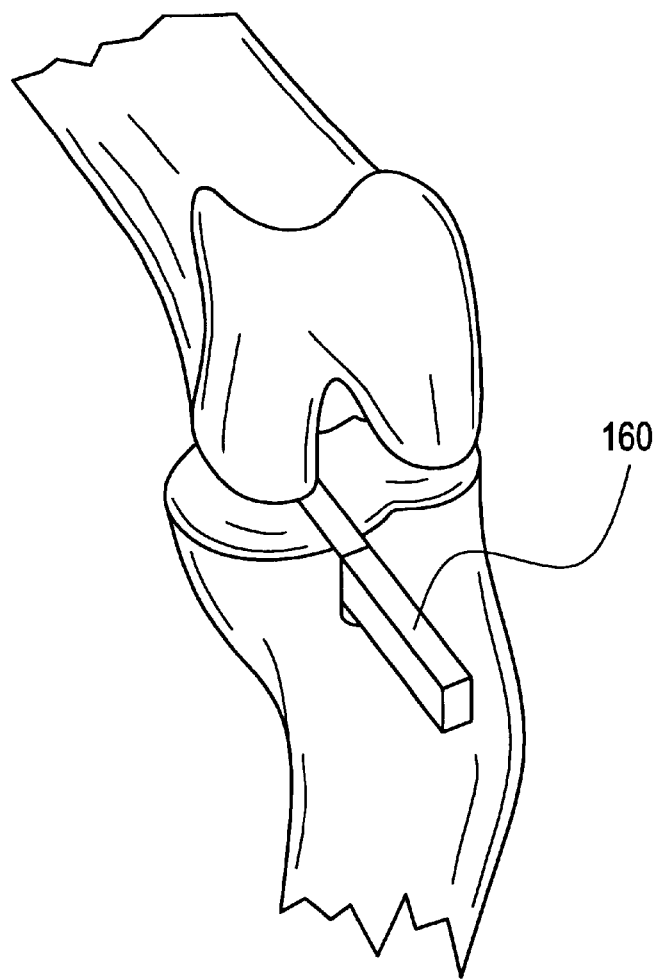
Figure 1F:
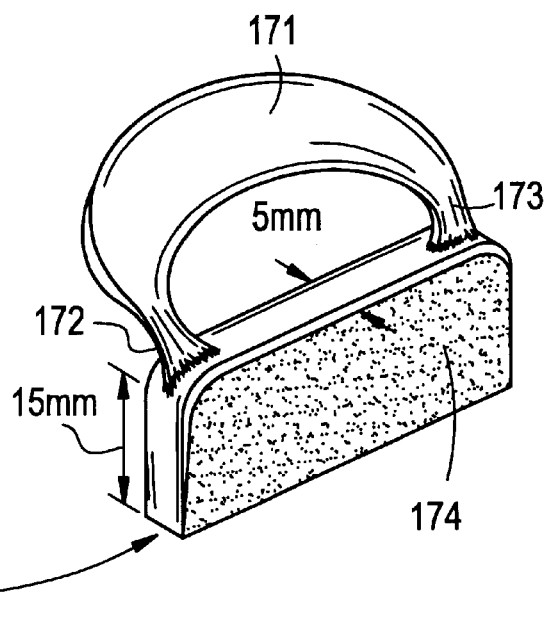
Figure 1G:
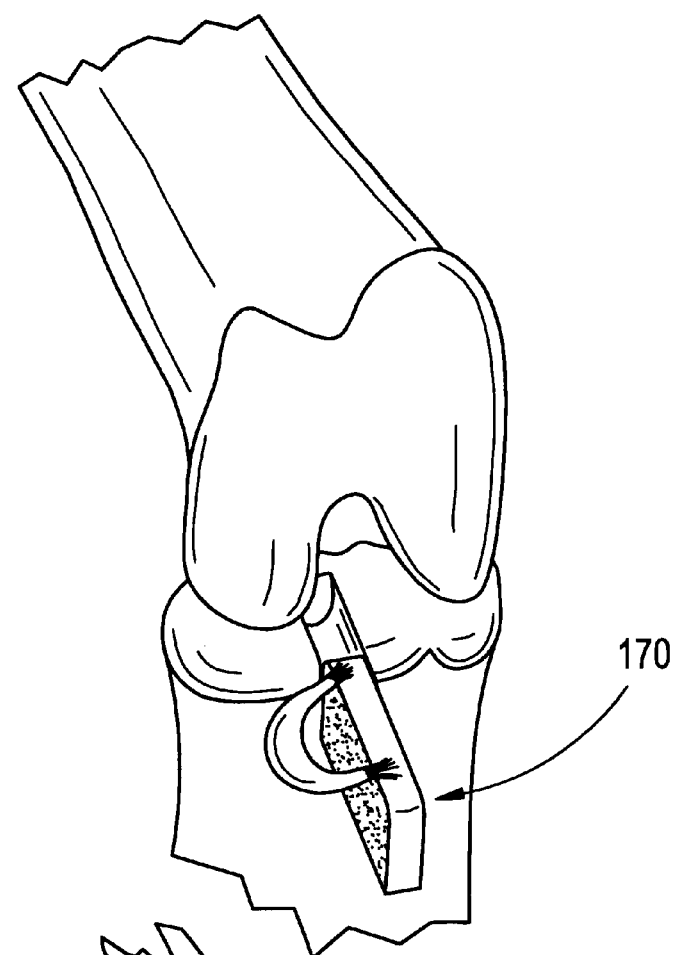
Figure 1H:
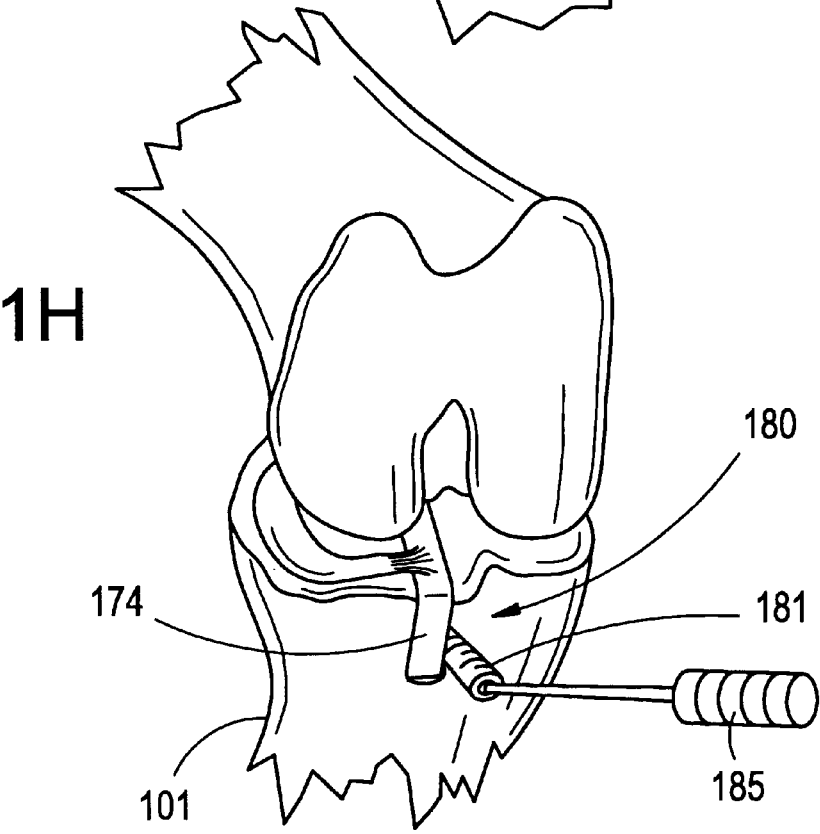

5. A drill guide is placed on the section of the straight rod extending anteriorly beyond the tibia. The guide, in a preferred embodiment, is designed to position a pin parallel to the tibial slope a specified distance below the reference slot. (In another embodiment, multiple pins are placed into the tibia in a row.)
6. A drill hole is made into the tibia using the drill guide.
7. A guide pin is placed into this hole. This pin has self-tapping tip which allows purchase of the posterior tibia.
8. The depth gauge and drill guide are removed.
9. A blind tunnel is created using a cannulated drill with a "stop" to prevent penetration of the posterior cortex.
10. A slot, 150, is formed between the blind tunnel and the reference slot, first using a cannulated drill bit over the guide pin (see FIG. 2C), and then using a cannulated box cutter. The slot, 150, is depicted in FIG. 1D.
11. The slot surfaces and dimensions are refined by use of one or more of a file, a rasp, straight and angled currettes, pituitary and custom rongeurs, or other means. This is depicted using a sizing rasp, 160, in FIG. 1E. This is etched within millimeter markings to further assess slot AP depth.
12. A sized meniscus implant, 170, such as is depicted in FIG. 1F, having a meniscus, 171, with both ends, 172 and 173, attached to opposite ends of a bone bridge, 174, where the bone bridge is shaped to fit into the slot of the sizing tray which would correspond to the slot formed in the tibia. This allows "presizing." Referring to FIG. 1G, a sized meniscus implant, 170, is slid into the slot, 150, and is aligned as needed.
13. The bone bridge, 174, is securely attached to the adjacent tibia bone, 101, at at least one point, 180. This is depicted in FIG. 1H where a bone screw, 181, is inserted between the bone bridge, 174, and the tibial point, 180, with a screwdriver, 185, securing the bridge by interference fit. Alternatively, the bridge may be held into place by sutures anchored over bone hole.

Thereafter, the soft tissue portion of the meniscal transplant is secured in a standard repair fashion and the site is properly closed.

One advantage of the present invention is having uniformly sized bone bridge sections of implants. This allows for standard sizing of the slot in the tibia, less custom fitting during an operation, and overall improved efficiency. It is noted that in one preferred embodiment, the width of the bone bridge is approximately 7 mm, the depth of the bone bridge is approximately 10 to 15 mm, the slot width is approximately 8 mm, and the slot depth is approximately 10 to 15 mm. This allows the bridge to smoothly slide into place and avoid the occasional bridge fracture that may occur when using a press fit requiring impaction for insertion.

In addition to embodiments of the methods of meniscus shaping and meniscus transplantation described above, apparatuses, described below, are used and claimed in the present invention.

Figure 2A:
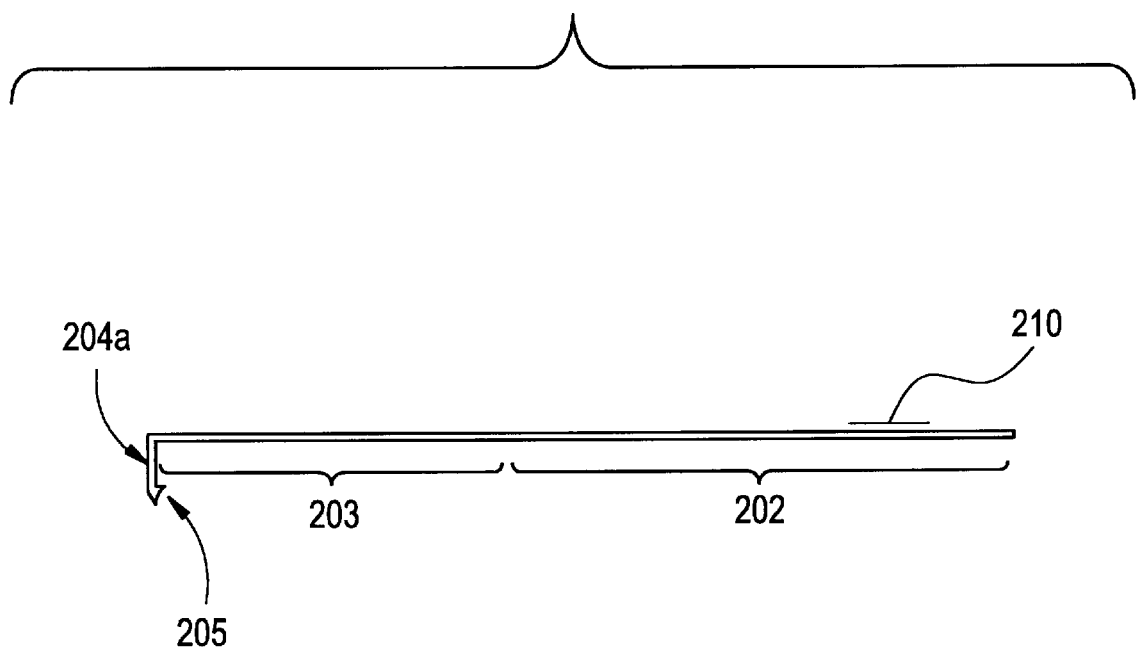
FIG. 2A is a side view of two embodiments of a depth gauge utilized in this invention.
Figure 2A:
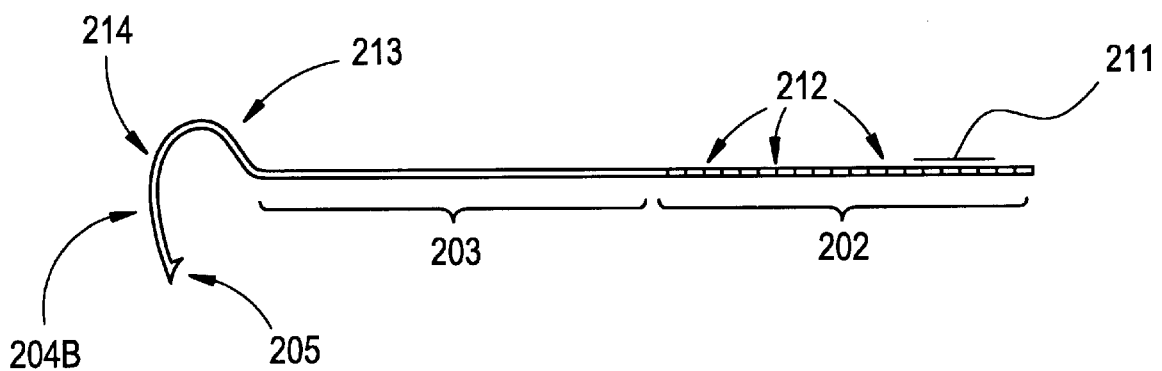

FIG. 2A provides a side-view representation of two embodiments of a depth gauge for use according to this invention. The non-looped gauge, 201, is comprised of an anterior section, 202, a slot section, 203, and a downwardly disposed posterior section, 204A. The anterior section, 202, optionally has spaced grooves, indentations, protrusions, or other means (not shown) over which a drill guide (not shown) can travel in intermittent increments. The posterior section, 204A, has at least one inwardly oriented tooth, spike or other grabbing or frictioning means, 205, known to those skilled in the art, which, during one aspect of operation, is used to temporarily attach to the adjacent bone to position the depth gauge.

The looped gauge, 211, is comprised of an anterior section, 202, a slot section, 203, and a downwardly disposed posterior section, 204B. The anterior section, 202, optionally has spaced grooves (shown as 212), indentations, protrusions, or other means over which a drill guide can travel in intermittent increments. The posterior section, 204B, has a distinct upward curve, 213, followed by a descending section, 214, the latter having at least one inwardly oriented tooth, spike or other grabbing or frictioning means, 205, known to those skilled in the art, which, during one aspect of operation, is used to temporarily attach to the adjacent bone to position the depth gauge. The looped curvature of the posterior section, 204, allows the apparatus to be placed properly in the reference slot, made in accordance with the method described herein, when the reference slot is not made in the posterior cortex of the tibia.

Figure 2B:
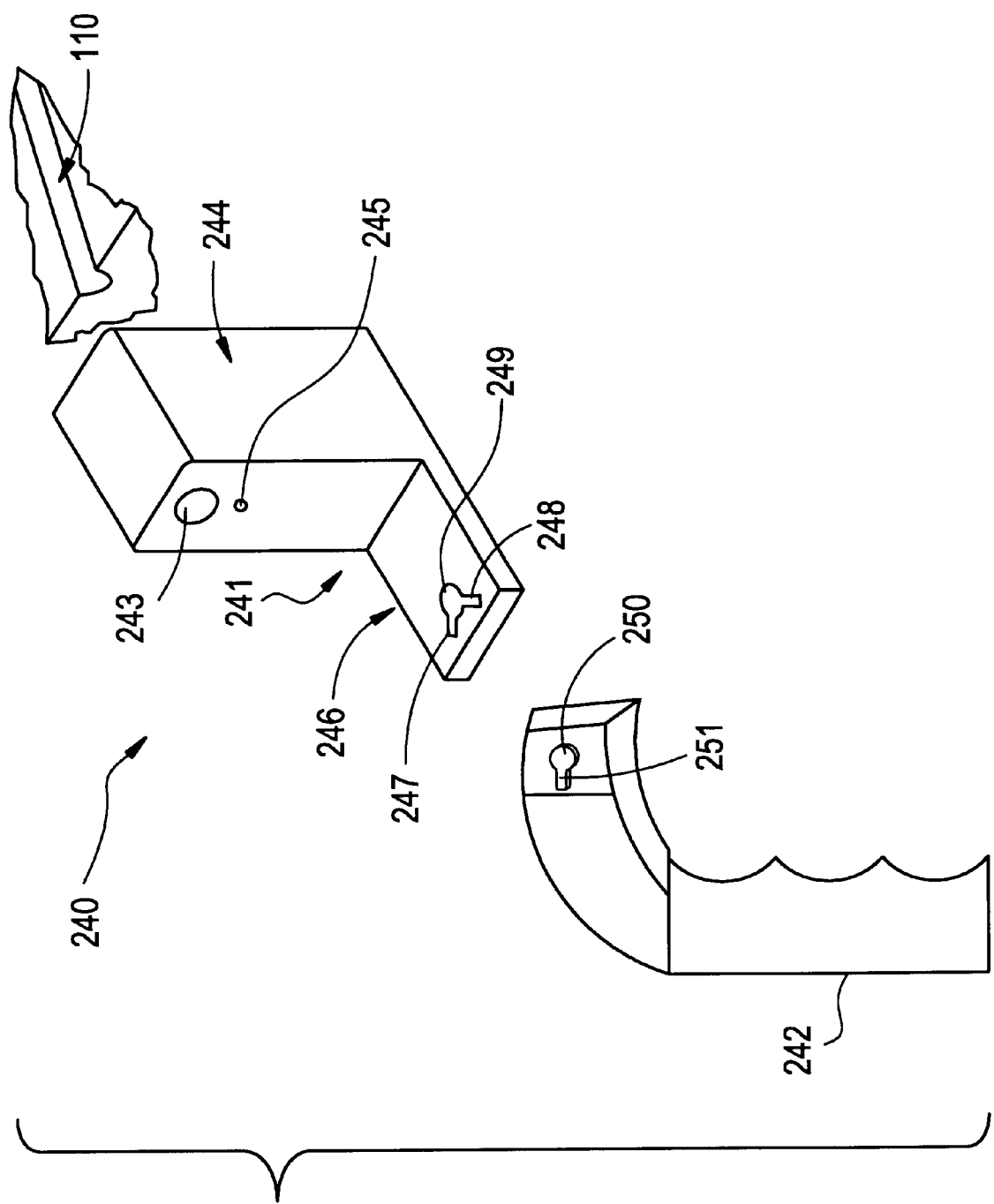
FIG. 2B is a perspective view of one embodiment of a drill guide utilized in this invention.

FIG. 2B shows one embodiment of a drill guide, 240, which is used to position a hole a specified distance below the linear superficial reference slot, 110, wherein, critically, the hole matches the front-to-rear angle of the slot. A base, 241, and a handle, 242, comprise the drill guide, 240. The base comprises an upper alignment tunnel, 243, which is sized to slide over the anterior section, 202 (of a gauge, 201 or 211) such that the proximal end, 244, of a drill guide hole, 245, abuts or is adjacent to the front of the tibia (not shown). In a preferred embodiment, the upper alignment tunnel, 243, is held in place on the anterior section, 202, by a spring-biasing mechanism that reversibly locks the drill guide, 240, into a set position (not shown). Other means as known in the art may be utilized to tension the drill guide, 240, in a position on the anterior section, 202, during the drilling operation.

At least one drill guide hole, 245, is positioned directly below the upper alignment tunnel, 243. In the preferred embodiment, the center-to-center distance between the upper alignment tunnel, 243, and the drill guide hole, 245, is approximately 4 to 5 mm, and the drill guide hole, 245, is sized to accept a drill bit for the drill pin hole size, which has a 0.093 inches diameter. Taking into account the depth of the slot and shape of the depth gauges, 201 and 211, these dimensions provide for a finished slot approximately 10–12 mm deep from the top of the tibia.

The drill guide preferred embodiment also has a handle entry hole, 246, positioned below the drill guide hole, 245, and having a first slot, 247, and a second slot, 248, one to either side of a central opening, 249. A handle, 242, having a post, 250, and one key or prominence, 251, affixed to one position on the post, 250, inserts into the handle entry hole, 246. The handle entry hole, 246, and the handle, 242, are designed such that a surgeon can position the handle for either right or left hand use. For instance, a right handed surgeon wanting to use his or her left hand on the handle would slide the handle 242, such that the key, 251, is to the right side of the handle entry hole, 246.

In operation, the surgeon positions the drill guide, 240, over the anterior section, 202, of a gauge, 201 or 202. Once the drill guide, 240, is properly aligned, a drill hole is made using the drill tube, 245, as alignment for a drill bit. As noted previously, the drill hole is made a predetermined distance into the tibia. The drill bit is removed and a self-tapping pin, 252, is inserted into the hole. Then a cannulated drill bit, 253, is placed around the pin, 252, and a wider hole is made using the pin as the guide. The cannulated 7 or 8 mm drill bit has a stop to allow a blind tunnel to be formed, i.e., the posterior cortex remains intact. The posterior cortex remaining intact allows the pin to remain with posterior cortex purchase and posterior structures are not exposed to the drill bit. The slot 150 is then formed with the blind tunnel forming the bottom of the slot. Alternatively, the wider drill bit can be drilled directly over the drill pin. With the pin remaining in position, the cannulated "box chisel" may be used to remove bone between the blind tunnel and the reference slot, thus forming the final slot 150.

Figure 2D:
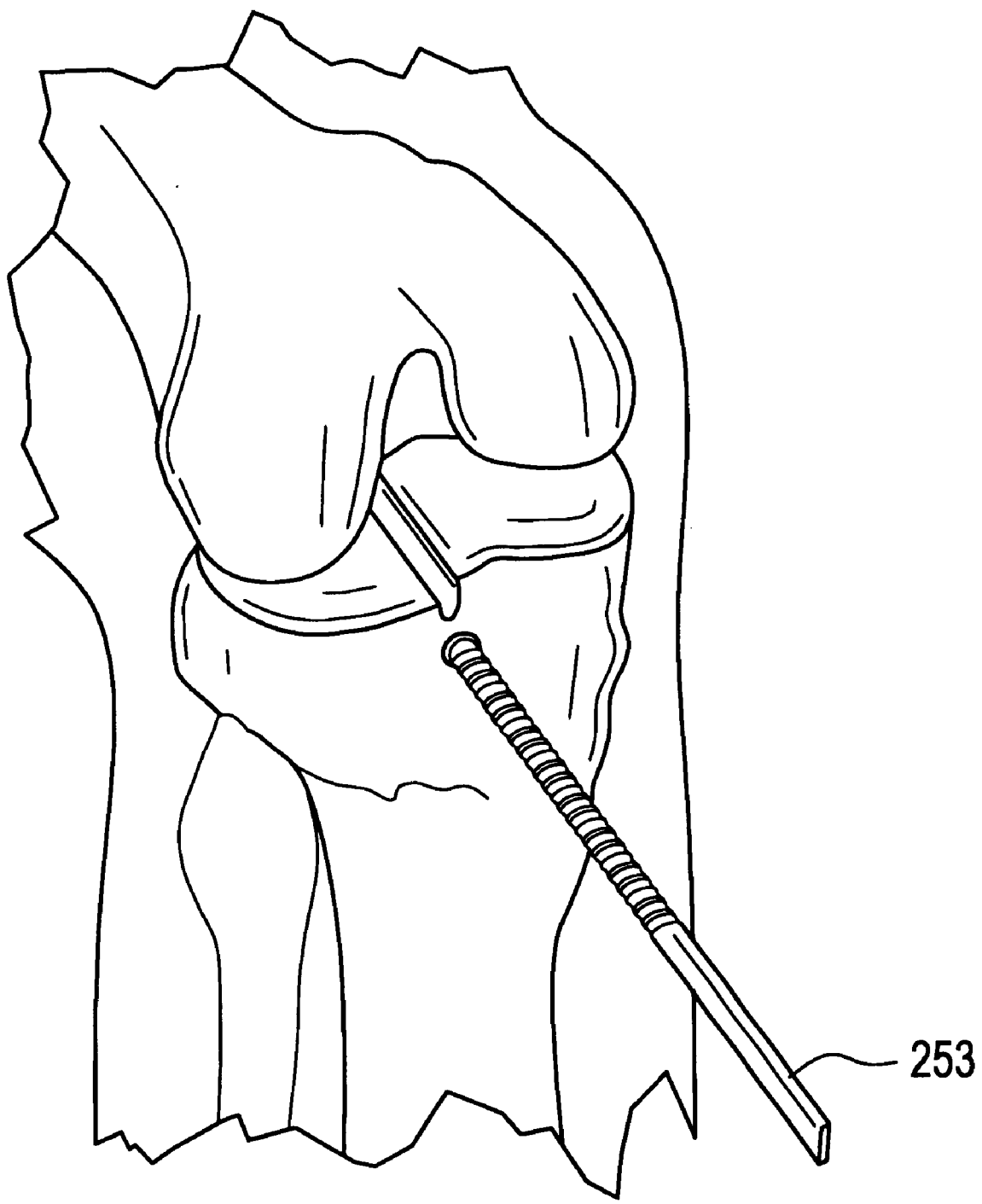
FIG. 2D is a perspective view of a cannulated drill bit over drilling a pin positioned in a hole formed by a drill guide according to this invention.

Additional drill guide holes may be placed one over the other in other embodiments. For instance, when a surgeon want to make a longer slot, for instance 15 mm from top to bottom, a second drill guide hole, 254, is placed below the drill guide tube shown in FIG. 2B. FIG. 2C shows one such embodiment, where drilling into the tibia using a second drill guide tube will result in a slot approximately 15 mm in height. FIG. 2D shows a cannulated drill bit, guided by a pin placed into a tibia, over drilling the pin to define the bottom portion of the slot.

By such use of the drill guide 240, the slot 150, when completed, is parallel to the slope of the tibia because the bottom of slot 150 matches the slope of the tibia. This results in the meniscus implant fitting uniformly at its top, conforming to the contour of the top of the tibia. This represents a significant advance in positioning a meniscal bone bridge to the tibia.

Figure 3:
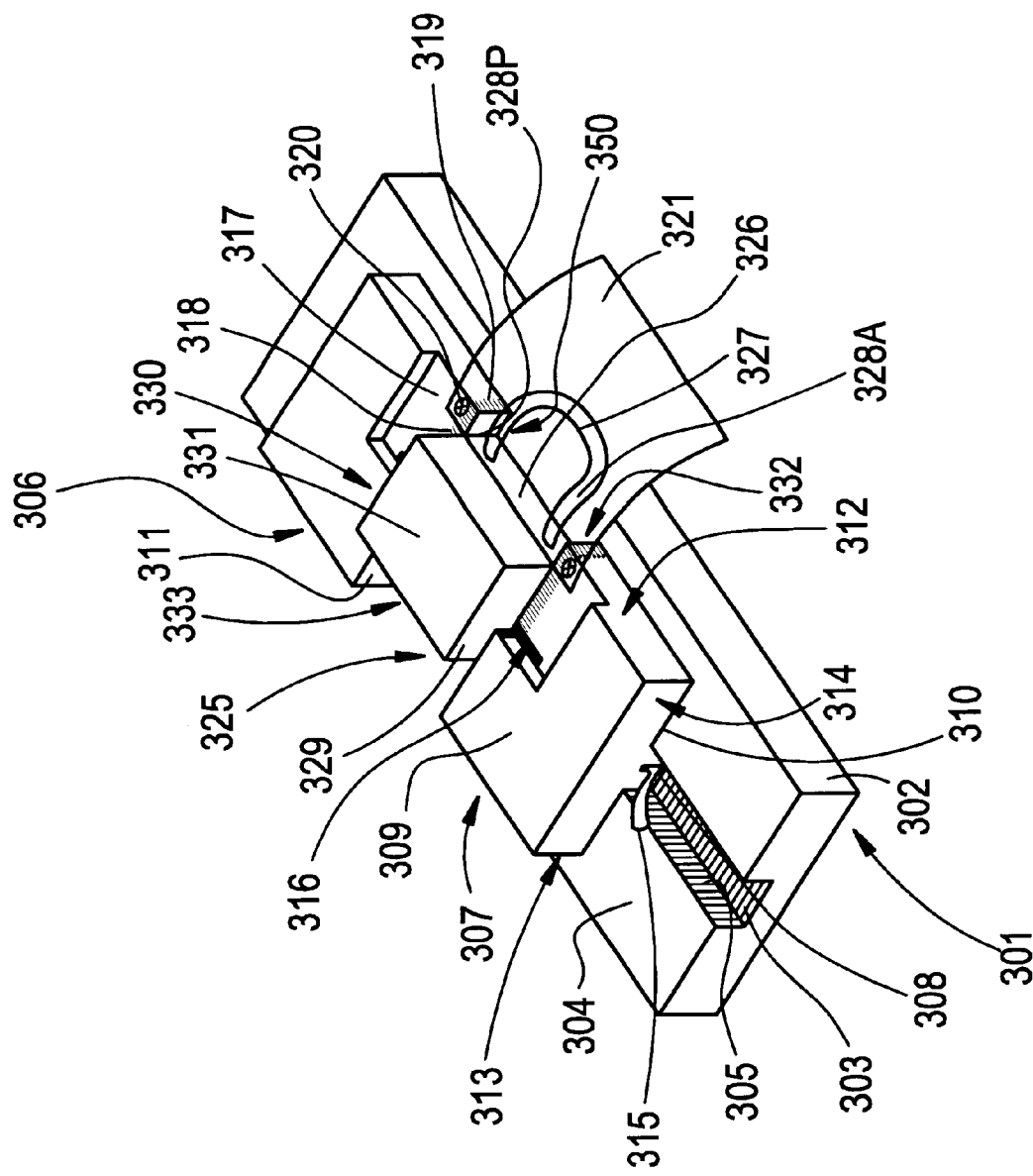
FIG. 3 is a perspective view of an apparatus for cutting the bone bridge of the implant to a specified size.

FIG. 3 provides a perspective view of a meniscal bridge cutting block (hereafter, 'MBCB'), 301, also referable to as bone sizing apparatus. The MBCB is for cutting the bone bridge to size to fit the slot made in the bone according to the method described herein. A base plate, 302, is generally rectangular and has a channel, 303, on its top surface, 304, the channel having spaced ribs, 305, along its bottom surface for ratcheting purposes. In a preferred embodiment, the channel extends partially, but not entirely, across the top surface. Positioned atop the base are two bone braces, 306 and 307. In a preferred embodiment, one bone brace, 306, is a fixed brace, and the other bone brace, 307, is a movable brace that has a lower extension, 308, which moves slidably in the channel. Each brace has a top surface, 309, a bottom surface, 310, coplanar and in proximity with the base top surface, 304, an inner face, 311, a front side, 312, a rear side, 313, and an outer side, 314. A ratchet release, 315, on the side of the movable brace, 307, engages with the spaced ribs, 305, to hold this brace temporarily in a desired position. In a preferred embodiment the inner faces, 311, of both braces, 306 and 307, are textured to provide a friction-based stability to position, and to hold during cutting, a bone bridge, 325. This helps grip the bone bridge, 325, and contributes to securing it in a suspended position, above the base's top surface, 304, as needed.

The two bone braces, 306 and 307, each have a saw capture slot, 316, extending through each brace from the top side, 309, toward or to the bottom surface, 310, and extending laterally, perpendicular to a plane defined by the inner face, 311, for a set distance from the inner face, 311. This slot is sized to receive a saw blade that makes a perpendicular cut into bone placed between the inner faces, 311.

Between the saw capture slot, 316, and the front side, 312, on the top surface, 309, each brace has a recessed rectangular area, 317, against which is positioned an oscillating saw. These recessed areas, 317, have spaced distance markings, 318, such as in millimeters, used to measure dimensions during the cutting operations. The front face, 312, below the recessed area, 317, also has spaced distance markings, 319, for the same purpose. Near the edge defining the border of the top surface, 309, and the front side, 312, each brace has a fastening means, 320, to demountably fasten a protective plate, 321.

In operation, the bone bridge, 325, with an attached meniscus, 327, is obtained from an allograft or xenograft donor. The bone bridge, 325, in FIG. 3 has a superior end, 326, bearing the meniscus, 327, the anterior horn attachment, 328A, and the posterior horn attachment, 328P, an anterior side, 329, a posterior side, 330, a medial side, 331, a lateral side, 332, and an inferior end, 333. The bone bridge, 325, is provided in a dimension exceeding the distance between the saw capture slot, 316, and the front sides, 312. The bone bridge, 325, is placed between the inner faces, 311, of the two bone braces, 306 and 307. The movable brace, 307, is moved inward to snug the bone bridge between the inner faces, 311. The ratchet, 315, locks the movable brace, 307, to compress the bone bridge, 325, between the braces, 306 and 307. The protective plate, 321, for instance a 0.2 mm thick rectangular plastic piece, is engaged into the two fastening means, 320, to cover and protect that meniscus, 327, during the cutting operations.

Generally, prior to insertion in the MBCB, the bone bridge, 325, is trimmed by hand, using tools known in the art, in order to smooth irregularities to the sides that are first positioned against the inner faces, 311. In the example in FIG. 3, these are the anterior and posterior sides, 329 and 330, respectively. This allows firm and even capture to the faces, and better assures a stable positioning. However, it is noted that for the preferred embodiment the bone is not trimmed adjacent to the anterior horn attachment, 328A, and the posterior horn attachment, 328P. These remain largely unchanged in overall length during this sizing procedure. It is particularly noted that the bone adjacent to the anterior horn attachment of the medial meniscus should not be trimmed, due to recognized variability in the horn attachment position. As noted herein, these areas are trimmed during final positioning of the bone bridge into the tibial slot.

In a preferred method, the bone bridge, 325, is suspended above the base by a desired distance (see gap, 350, in drawing). This results in the cut to the opposite side establishing the side-to-side final thickness.

Having so positioned the bone bridge, 325, the first cut is to remove bone from the top-facing side of the bone bridge in its current position. In FIG. 3, this is shown as the medial side, 331. (However, it should be appreciated that other sequences of cuts may be made in accordance with the present invention, and the sequence provided herein is merely exemplary.) An oscillating saw fits into the recessed area, 317, and cuts away a desired quantity of bone to reduce the width of the bone bridge. Then the ratchet, 307, is released to loosen the bone bridge, 325, which is rotated 180 degrees to expose the opposite side to the top. After proper measurement to set the desired width, and positioning against the inner faces, 311, of the braces, 306 and 307, this side is similarly cut with an oscillating saw (not shown). Preferably, the bone bridge, 325, is suspended under compression between textured inner faces, 311, of the braces, 306 and 307, the compression being set by the ratchet release, 315, engaging between the spaced ribs, 305.

The spaced distance markings, 319, help determine the in-process and final width of the bone bridge, 325. When a thinner bone bridge is desired, various means exist for cutting this. In addition to the suspension means, as described above, a flat spacer can be placed beneath the bone bridge, thereby raising it, so less space is present between these cut sides. This may be more important where the inner faces, 311, are not sufficiently textured, or less compression is placed on the bone bridge, 325, by the inner faces, 311. Obviously, during all cuts near the meniscus, 327, care is taken to avoid damage to the meniscus, 327.

Next, measurement and, as needed, adjustment is made to position the bone block such that the desired height, e.g., 15 mm., is the distance between the superior end, 326, (where the meniscus is attached) and the nearest edge of the saw capture slot, 316. The movable brace compresses the bone block, and the ratchet, sliding between two ribs, secures the bone bridge under compressive force. Then a saw blade is placed inside one of the slots, 316, and the saw blade cuts across the bone block, 325, to the slot, 316, on the opposing brace. As noted, this establishes the desired height of the bone block.

The above operations using the MBCB, 301, may take place at a centralized processing center that produces one or more standard sizes of bone bridges. Also, the MBCB, 301, may be used prior to or during a specific surgical procedure, either to cut from a previously un-sized bone bridge, or to make final modifications as needed for the specific surgical procedure.

As described above, a significant aspect of the present invention is how the reference slot bottom is made to conform to the tibial plane anterior/posterior slope (referred to as the tibial slope). This is achieved by visually comparing the reference slot wall height above the depth gauge that is inserted in the reference slot. The comparison is done where the surrounding bone contour is coplanar with the tibial plane (e.g., not where the tibial spine has been removed for the reference slot, but toward each of the ends of the reference slot). After sufficient leveling, the final visual comparison indicates the reference slot bottom is basically in line with the angle of the tibial plane anterior/posterior slope. Obtaining this slope is critical, because this determines the slope of the bottom of the slot, which in turn affects how the top of the bony bridge, with its meniscus horn attachments and meniscus, aligns with the tibia. All of these alignment factors contribute to a good fit and structural integrity that contribute to a higher percentage of successful long-term surgical outcomes.

In preferred embodiments of the present invention, the reference slot, the slot for the bone bridge, or both, are made to not extend through the posterior cortex of the tibia of the recipient. This is accomplished, for example, by setting the proper stops on the apparatuses used for making the slot on the tibia. The primary reason for not drilling through the posterior cortex of the tibia is to avoid damage to nerves and vessels exterior and posterior to the tibia. Another reason for not cutting into the posterior cortex is to avoid having bone debris on the posterior tibia area, away from ready access for removal during the operation.

In a preferred embodiment of the present invention, during placement of the bone bridge in the tibial slot, the top of the bone bridge is aligned to be flush with the plateau of the tibia. This contributes to the alignment of the meniscus. One means to assist final positioning is to place one end of a surgical spatula or other long flat device into the slot, between the bone bridge and the slot bottom surface, and lever upward on the posterior lower end of the bridge to cause the posterior edge of the dorsal surface to elevate. The final position is then adjusted with the surgical spatula superior or inferior to the bone bridge as needed. This can be supplemented by gently tamping the bridge down in the slot, prior to tapping the slot or screw hole and fixing the bone bridge in place with a pin or screw.

A series of steps of the method of this invention are described below, with variations and details provided.

1. Positioning

As a preliminary step, the limb undergoing surgery is positioned. A meniscus allograft replacement is typically either performed as an independent surgery or in conjunction with additional knee restoration techniques. When performed independently, the meniscus may be inserted arthroscopically. If the surgery is performed in conjunction with other cartilage restoration techniques, the procedure may often be performed in an open manner.

Whichever technique is planned, the surgeon's preference of using a limb holder or unsupported limb is at their discretion. Care should be taken such that there is free access to the posterior medial and/or posterior lateral corners of the joint to allow adequate room for an incision to the level of capsule when employing the inside out technique of suturing the allograft meniscus.

2. Exposure a. Arthroscopic:

For portal selection at the involved compartment, a spinal needle is inserted through the skin so it will course over the anterior horn of the meniscus and then proceed to the posterior horn. This is typically not a "standard" anteriomedial or anteriolateral portal site. The purpose of placing the portal directly in line of the meniscal horns is to allow direct "in line" access to the posterior horn. This portal will be used for insertion of the guides. Accessory portals medial or lateral to this site (that is, more standard utility portals) may be utilized for probes, hand and power instruments to reach the other aspects of the meniscus and joint.

The portal is extended proximally and distally once the slot position is determined, as indicated below.

b. Open:

With open procedures, it is very common for the exposure to be a medial parapatellar arthrotomy. When full exposure of both condyles is necessary, it is often simpler to perform a tibial tubercle osteotomy, and then reflect the extensor mechanism proximal laterally. With careful planning of the osteotomy, this does not in any way interfere with the anticipated slot for placement of the bone bridge.

c. In Conjunction with High Tibial Osteotomy:

It is recommended that the osteotomy be performed first. This will allow the plane of the osteotomy to be known at the time of the slot formation. Furthermore, if the slot is created first, this may act as a stress riser that could fracture through to the osteotomy—whether the osteotomy is an opening wedge or a closing wedge type.

d. In Conjunction with Anterior Cruciate Ligament Reconstruction:

Anterior cruciate ligament ("ACL") reconstruction is often performed at the same setting. The tibial tunnel intersects the slot of a medial meniscus bone bridge. The sequence for this is to first form the ACL tunnel starting as far distal as possible without compromising anatomometric positioning of the ACL. Next, the slot is formed followed by inserting the bone bridge into the slot, and then carefully reaming out a portion of the bone bridge, which courses through the ACL tunnel. If properly planned, this does not compromise the ACL tunnel, the bone bridge or the slot.

3. Assessment of Meniscus Attachment Sites

The following papers, herein incorporated by reference, show standard and variant positions of meniscus horn attachments:

1. Nelson E W, LaPrade R F. The anterior intermeniscal ligament of the knee. An anatomic study. Am. J Sports Med. 2000 Jan–Feb; 28(1):74-6.
2. Berlet G C, Fowler P J. The anterior horn of the medical meniscus. An anatomic study of its insertion. Am. J Sports Med. 1998 Jul–Aug; 26(4):540-3.
3. Ohkoshi Y, et al. Arthroscopic studies of variants of the anterior horn of the medical meniscus. Arthroscopy. 1997 Dec; 13(6):725-30.

Typically, the meniscus horn attachments are visible even after menisectomy as remnant attachments. Also, even after an arthroscopic "partial menisectomy", even though the meniscus is absent from a biomechanical standpoint, the anterior horn is usually intact and the attachment site posteriorly has fibers left as they course into the tibia.

With knowledge of these attachment sites aiding direct observation, an electrocautery or thermal device is then used to connect the center aspect of the posterior horn attachment to the center aspect of the anterior horn attachment. All horn attachments are usually discrete sites—except the medial meniscus anterior horn. Unlike the other horns, for this horn there is marked variability. In addition, there can be confusion over the contribution of the "intermeniscal ligament" or bands attached to the superficial surface of the meniscus that then course laterally. These bands are accessories. The attachment site is deep to these structures. In most cases, the attachment inserts into bone at the anterior aspect of the tibial plateau. This is in distinction to the other horn sites, which attach on the superior aspect of the plateau, rather than the anterior aspect.

Care is taken on the medial meniscus to be medial enough such that the slot initially will not enter the PCL fossa. The anterior and posterior cruciate ligaments are protected at all times, as are the margins of the condyles. Time taken to clear debris early in the procedure makes all subsequent steps easier.

4. Development of a Superficial Reference Slot

Using the straight line formed above, which will not be in the sagittal plane, but rather skew to it, a 4 mm burr is used to form a straight superficial reference slot anterior to posterior, keeping level to the plane of the plateau. The tibial spine is removed along this line as necessary to afford a straight anterior to posterior slot in the plane of the tibial slope. Matching the gentle anterior to posterior slope of the tibial plateau (referred to as the 'tibial slope') is accomplished first by observing the 4 mm burr as it is creating the slot. When the burr head is "buried" in the slot to the point that the top of the burr is even with the subchondral bone, then the reference slot matches the plane of the tibial plateau. This is only at the region anterior and posterior to the spine. The match of the tibial plateau slope is further checked with the depth gauge. The gauge should sit evenly in this superficial reference slot, that is, it does not rock up or down in the slot-it lies flat in the slot.

5. Depth Gauge and Drill Guide Attachment

When the depth gauge has been determined both to be in the line defined by the meniscal horns and to lie in the plane of the tibial plateau, the depth gauge is engaged in the posterior cortex of the tibial plateau. In a preferred embodiment, the shallow reference slot extends to, but does not penetrate the posterior tibial cortex. A rise in the posterior aspect of the depth gauge allows the gauge to take into account this retained posterior aspect of the tibia. The depth gauge has a pointed hook to engage in the posterior cortex under direct visualization. Traction is applied on the depth gauge to maintain its position while the drill guide is inserted onto the anterior aspect of the depth gauge. This anterior aspect of the depth gauge has teeth or grooves providing a ratcheting effect. The drill guide is ratcheted over the depth gauge and pushed directly to the anterior aspect of the tibia. Care is taken at this point to assure that the length of the depth gauge has remained flush in the superficial reference slot. Thus, by having the depth gauge duplicate the slope of the tibial plateau and be in line with the horn attachments, the final slot established with the drill guide achieves the same orientation.

6. Drilling the Blind Tunnel to Establish the Depth of the Slot

Drilling through the drill guide, the drill bit stops at a depth predetermined by the depth gauge, so as to not penetrate the posterior cortex. In a preferred embodiment, the drill bit is removed and a free guide pin with self-tapping tip is inserted into the hole created by the drill bit. The depth gauge and drill guide are removed. A cannulated 7 or 8 mm drill bit is then used to over-drill over the free guide pin. This creates a blind tunnel in line with the meniscal attachment sites and in line with the slope of the tibial plateau. The blind tunnel does not penetrate the posterior cortex. The guide pin remains purchased to the posterior cortex (tibial).

7. Final Slot Creation

The position of the blind tunnel created is critically assessed. Adjustments may be made as necessary before the final slot is created. At this point in the process a small amount of bone normally lies between the blind tunnel and the superficial reference slot. When the tunnel position is determined to be in proper alignment, a 7 or 8×10 mm cannulated box chisel is used to remove the bone between the tunnel and the reference slot. This creates vertical walls and opens the roof of the slot. The final slot is further prepared posteriorly with angled curettes to the level of the cortical bone, but not through the posterior cortical bone. A 7 or 8×10 mm sizer rasp is inserted, and this smoothes and assures that the bone bridge enters smoothly.

In one embodiment, the drill guide is designed so that when used in conjunction with a 4 mm superficial reference slot the total final slot depth is approximately 10–12 mm—after the bone lying between the blind tunnel and the reference slot is removed. Although the typical application is expected to use a 7 mm wide bone bridge in an 8 mm wide slot (and the height of the bone bridge is approximately 10–15 mm), in some cases a surgeon may believe the slot should be narrower or wider. In such cases, appropriate sized cannulated drill bits, box chisels and sizer rasps can be employed.

8. Preparation of the Allograft Meniscus

The allograft meniscus is given a final pre-implantation assessment and preparation. If the meniscus bone bridge is supplied to the surgery site pre-shaped, then only confirmatory measurement and minor adjustments may be required during the surgical event. When preparation is required at the surgical event, if there is a large bony attachment, this must be trimmed. This can be accomplished by first moving the meniscus back and forth about the attachment sites such as moving a bucket handle back and forth. This allows a dynamic appreciation of the true meniscal horn attachments as opposed to connective tissue not truly participating in the attachment. The accessory soft tissue attachments are debrided, leaving only the firm true horn attachments that are usually 5–6 mm in width. The posterior horn of the medial meniscus and both horns of the lateral meniscus are usually easy to identify in this manner. It is useful to mark out the straight lines connecting the planned cuts medial and lateral to the horn attachments.

During this first cut, the bone bridge is maintained at a uniform 6–7 mm width. The supplied bone block attached to the allograft meniscus is often skew to this planned cut. Therefore care is taken to assure that the shape of the allograft bone block does not influence the cuts made to establish the width of the meniscus.

A second cut establishes the depth of the bone bridge. This is measured at the horns and not at the spine area. Depths are cut to be 1 mm less than the depth of the final slot. The cartilage covering the spine area normally is not implanted and can be removed to allow better visualization during insertion.

A third cut removes small amounts of bone that extend posterior to the posterior horn attachment. Removing this allows placing the bone bridge to the posterior extent of the slot without breaking through the posterior cortex.

The bone bridge is then placed in the bone bridge sizing plate to assure it fits smoothly into the final slot. A bone bridge sizing plate is a device having slots of differing widths, into which a bone bridge may be inserted to determine the width of the bone bridge. If it does not properly fit, then the bone bridge is meticulously trimmed to fit in the desired size opening.

It is noted that the anterior horn of the medial meniscus will at times present problems. The literature demonstrates the variability of the medial meniscus anterior horn. Some allografts have remnants of the "intermeniscal ligament" which should be debrided leaving only the true anterior horn attachment to bone. Unlike the other horn attachments, the anterior horn of the medial meniscus usually extends to the anterior-most extent of the tibial plateau for attachment. This is preferably left in situ. The extraneous attachments are removed leaving a 6–7 mm wide bone attachment. In rare cases in which the anterior attachment is 8 to 9 mm, then this region alone is left at 8 to 9 mm and the remainder of the bridge is trimmed to the desired 6 or 7 mm in width. Prior to insertion, for these exceptional embodiments, the anterior-most aspect of the slot is opened to accept this widened area.

Noting that the anterior horn attachment is on the anterior portion of the tibia, it bears emphasizing that care should be used when placing the transplant in the slot. Forcing the meniscus bony bridge into a slot with a bone tamp may injure the soft tissue or crumble the bone in that region. Thus, the present technique slightly undersizes the meniscal bone bridge width, for instance 6 mm width fitting into in a 7 mm final slot, and a 7 mm bridge in an 8 mm slot, thereby allowing gentle handling of the bone bridge as well as allowing for necessary adjustment of the anterior-posterior position.

9. Insertion and Fixation of the Meniscus

As the final slot has been smoothed and sized with a sizing rasp or like means, and the bridge has been sized to fit in the bone bridge sizer, the bone bridge should smoothly insert into the slot. Reducing the soft tissue portion of the meniscus is frequently the most challenging part of this procedure. Depending on the compartment, generalized laxity of the joint and potential contracture of ipsilateral ligaments over time from the loss of meniscal tissue, it may be necessary to perform limited releases to reestablish the joint space. To aid in positioning the soft portion of the meniscus, a temporary vertical mattress suture is placed in the posterior horn and then exits through the posterior knee incision where subsequent inside out sutures will exit. As the bone bridge is inserted, traction is applied to the posterior horn suture and a meniscal probe pushes the soft tissue portion of the meniscus while the joint is manually opened by stress to the knee applied by an assistant. In an ACL deficient knee, the tendency for the tibia to displace anteriorly causes added difficulty. It is necessary to manually position the tibia posteriorly.

Once the meniscus is reduced, the proper sizing and positioning is confirmed, as it remains in proper position while performing knee range of motion. The only position of the bridge to be determined is in the AP direction. When considering the biomechanical goal of duplicating hoop stress and aiding in transferring loads between the femoral condyle and tibial plateau, care is taken to match the meniscus to the femoral condyle as well as the tibial plateau. With a properly sized and positioned meniscus, both of these matches occur. At this point, the proper AP position is maintained while a guide pin is inserted between the bridge and central side of the slot. A tap creates a blind tunnel for an allograft interference screw to achieve final fixation of the bone bridge in the final slot. Alternatively, sutures may be used to anchor the bone bridge in the slot. Sutures are pulled through drill holes and tied over bone anterior on the proximal tibia. The meniscus is then fixed with vertical mattress sutures placed using inside out techniques or as per surgeon preference.

Having described steps of a preferred method, with variations, a further description of embodiments is provided. In one embodiment of this invention, after exposing the tibia proximal surface, a linear shallow groove, or reference slot, is made between and encompassing the anterior and posterior meniscus horn attachments. For instance, a 4 mm arthroscopic burr is employed, and the surgeon fashions a straight-line groove. In this process, additional material is removed from the tibial spine to create a reference slot with the object of having the bottom of the reference slot level and having the same anterior to posterior slope of a plane that is defined by the line between anterior and posterior horns of the meniscus. This slope angle, referred to as the tibial slope, is known to be variable among individuals. This further justifies use of the present method to match, during the meniscus implantation procedure, the tibial slope on a patient-by-patient basis. It has been recognized that duplicating this slope during the positioning of a replacement meniscus is an important factor in achieving a successful meniscus replacement. This is because duplicating this slope provides a more anatomical fit. The more anatomic the fit the better the duplication of meniscal function.

The surgeon may choose to preserve or remove the posterior wall (cortical) of the tibia; in a preferred embodiment the posterior cortical wall of the tibia is not removed. After a basic reference slot is established having a reasonably level floor, a depth gauge is inserted into the reference slot. The top of the gauge generally fits below the upper edges of the reference slot walls, and the surgeon compares by eye the relative distance, or gap, between the top edges of the depth gauge and the upper reference slot wall edges. If there is a disparity in the gap for the anterior versus the posterior end of the reference slot, the surgeon removes the guide, and removes additional bone material from the reference slot to better level the reference slot floor. The measuring with the guide and removal of bony material is repeated until the reference slot floor is flat and conforms, as indicated by the comparison of the gap along the reference slot from anterior to posterior, to the tibial slope.

After this is achieved, a guide, placed onto the front section of the depth gauge (the section extending anteriorly from the reference slot), is used to position a guide pin a specified distance distal on the anterior face of the tibia below the reference slot. The guide pin has depth markings so that it can be drilled to an appropriate depth when compared to the depth of the tibia on the depth gauge. Alternatively, the depth gauge also acts to stop the drill bit if a drill bit stop is applied rather than using direct sight; thus protecting nerves and vessels posterior to the knee. The guide, by attaching to the depth gauge, transposes the tibial slope angle to the angle at which the pin or drill bit is advanced into the tibia. The guide pin generally extends into the tibia up to but not through the posterior tibia cortex—it engages the cortex with a self-tapping tip. The tip maintains purchase even after the blind tunnel is created.

In a preferred embodiment, a single hole is made by a drill bit positioned by the drill guide, and a single drill pin is placed into that hole in the tibia. As an alternative, several drill pins can be inserted, each positioned at a specified distance apart. Once a guide pin is in place, it can be over-drilled with a cannulated drill bit. The drill bit serves to remove most of the bone to form the slot. After drilling, a cannulated box cutter is passed over the guide pin (which remains attached posteriorly) to remove remaining bone and to better form the slot. An appropriately sized sizer/rasp is then used to further clean and form the slot.

After the slot is formed, it is ready for implant insertion. The meniscus implant is obtained as a unitary piece, having been removed from an allograft or xenograft donor source, such as a human cadaver, bovine, ovine, equine, porcine, canine, or other allograft or xenograft bone source. A meniscus implant may be from one of these sources, and have been modified to become an artificial composite, e.g., having been integrated with SIS, CMI, etc. The implant comprises a bone bridge, which is a generally rectangular shape fittable into the slot, and a complete meniscus attached at two points, the anterior and posterior horn attachment points, on the superior end of the bridge.

In one embodiment, the bone bridge is milled to a standard size prior to surgery, where that size need not be further adjusted during surgery. Alternately, final sizing can be done just before or during surgery. One advantage of this invention is the pre-sizing and reduction of time in surgery spent on sizing of the replacement piece. Another advantage is the specific apparatus designed for sizing the bony bridge, which is described hereinafter.

After the bone bridge is slid into the slot, its superficial surface position is adjusted to a proper position for the meniscus in relation to the femoral condyle. An additional step is to bring the knee joint through a full range of motion to more optimally position the replacement meniscus in relation to the femoral condyle. It is noted that meniscus positioning adjustments with the keyhole technique are not as readily made as with the present invention, and typically adjustments by going through the full range of motion are not done. The bridge in slot allows final position adjustments prior to fixation. A screw hole is tapped on the central face of the bone bridge and the adjacent section of tibial bone. A pin, a screw or other means is used to secure the bone bridge in position with interference fixation purchase.

Although 1.0 mm clearances are generally used in the above examples to describe the difference between the dimension of the slot and the corresponding width or height of the bone bridge fitting therein, a preferred clearance has been identified as approximately 0.5 mm. This means that 0.25 mm clearance has been found preferred between each junction of a slot wall and a side of the bone bridge.

Those skilled in the art will appreciate that the graft may be an allograft, artificial composite or xenograft. Xenograft implants may further require treatments to minimize the level of antigenic agents and/or potentially pathogenic agents present in the graft. Techniques now known, or those which are later developed, for preparing tissue such that it is suitable for and not rejected by the recipient are incorporated herein. For instance, U.S. Pat. No. 5,972,368 and PCT publication number WO 00/29037 are incorporated herein. In cases where the graft is an allograft, a donor is preferably screened for a wide variety of communicable diseases and pathogens, including human immunodeficiency virus, cytomegalovirus, hepatitis B, hepatitis C and several other pathogens. These tests may be conducted by any of a number of means conventional in the art, including, but not limited to, ELISA assays, PCR assays, or hemagglutination. Such testing preferably follows the requirements of the following associations: (a) American Association of Tissue Banks. Technical Manual for Tissue Banking, Technical Manual-Musculoskeletal Tissues, pages M19–M20; (b) The Food and Drug Administration, Interim Rule, Federal Register, Vol. 58, No. 238, Tuesday, December 14, Rules and Regulations, 65517, D. Infectious Disease Testing and Donor Screening; (c) MMWR, Vol. 43, No. RR-8, Guidelines for Preventing Transmission of Human Immunodeficiency Virus Through Transplantation of Human Tissue and Organs, pages 4–7; (d) Florida Administrative Weekly, Vol. 10, No.34, Aug. 21, 1992, 59A-1.001-014, 59A-1.005(12) (c), F.A.C., (12)(a)–(h), 59A-1.005(15, F.A.C., (4) (a)-(8). In addition to a battery of standard biochemical assays, the donor, or their next of kin can be interviewed to ascertain whether the donor engaged in any of a number of high risk behaviors such as having multiple sexual partners, suffering from hemophilia, engaging in intravenous drug use etc. Once a donor has been ascertained to be acceptable, the tissue for the meniscus implant as described above is recovered and cleaned.

The teachings of all patents and publications cited throughout this specification are incorporated by reference in their entirety to the extent not inconsistent with the teachings herein.

It should be understood that the examples and embodiments described herein are for illustrative purposes only and that various modifications or changes in light thereof will be suggested to persons skilled in the art and are to be included within the spirit and purview of this application and the scope of the appended claims. Having described this invention, including the best mode thereof, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein. Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

What is claimed is:

1. A kit for use in shaping and implanting a meniscal implant, comprising
   a. a bone bridge sizer for reshaping the bone bridge on a meniscal implant into a slotted shape; and
   b. instructions for use of said bone bridge sizer to cut said bone bridge of a tibial meniscus implant to a predetermined size and shape suitable for implantation into a correspondingly sized rectangular slot on the dorsal surface of a human tibia.

2. The kit according to claim 1, additionally comprising a drill pin and a cannulated drill bit sized to fit over said drill pin.

3. The kit according to claim 1, additionally comprising at least one pre-sized meniscus implant.

4. The kit according to claim 1, additionally comprising a pre-sized meniscal implant for aligning and implanting on the dorsal surface of a human tibia, said meinscal implant comprising an allograft or xenograft tibial meinscus having two opposing ends, said opposing ends being attached to opposite ends of a bone bridge, wherein said bone bridge is shaped to fit into the slot of a sizing tray, said sizing tray corresponding in size and shape to the slot formed on the dorsal surface of said tibia.

5. The kit according to claim 1, additionally comprising a tool to size a slot in a tibia bone selected from the group consisting of a slot sizer, a rasp, and a box chisel.

6. The kit according to claim 5, additionally comprising a depth gauge fittable into said slot in said tibia and having indicia thereon for indicating the depth of said slot.

7. The kit according to claim 6, additionally comprising a drill guide fittable over said depth gauge when said depth gauge is positioned in said slot and when so fitted, providing a guide for drilling at least one hole a specific distance and position from said slot.

8. A kit for implanting a meniscus on the dorsal surface of a human tibia in need of a meniscus, comprising (a) a pre-sized and pre-shaped meniscal implant for aligning on the dorsal surface of a human tibia, said implant comprising an allograft or xenograft tibial meniscus having two opposing ends, said opposing ends being attached to opposite ends of a bone bridge, wherein said bone bridge is pre-sized and pre-shaped to fit into a correspondingly sized slot formed on the dorsal surface of said human tibia, said bone bridge and said meniscus being a unitary piece; and (2) at least one tool to assist in implanting said meniscus on the dorsal surface of said human tibia.

9. The kit of claim 8, wherein said at least one tool a depth gauge.

10. The kit of claim 8, wherein said at least one tool is a drill guide for drilling at least one hole a specific distance and position from said sized slot.

11. The kit of claim 8, wherein said at least one tool is a slot sizer.

12. The kit of claim 8, wherein said at least one tool is a rasp.

13. The kit of claim 8, wherein said bone bridge is 6 to 7 mm wide.

* * * * *